(12) United States Patent
Shah et al.

(10) Patent No.: US 9,107,835 B2
(45) Date of Patent: Aug. 18, 2015

(54) CHEWABLE ENTERIC COATED ASPIRIN TABLETS

(71) Applicant: MCNEIL-PPC, INC., Skillman, NJ (US)

(72) Inventors: Manoj N. Shah, Norristown, PA (US);
James S. Beahm, Exton, PA (US);
Robert Shen, North Wales, PA (US)

(73) Assignee: McNeil-PPC, Inc., Skillman, NJ (US)

( * ) Notice: Subject to any disclaimer, the term of this patent is extended or adjusted under 35 U.S.C. 154(b) by 0 days.

(21) Appl. No.: 14/274,853

(22) Filed: May 12, 2014

(65) Prior Publication Data

US 2014/0248352 A1      Sep. 4, 2014

Related U.S. Application Data

(62) Division of application No. 10/961,563, filed on Oct. 8, 2004, now Pat. No. 8,758,814.

(51) Int. Cl.
*A61K 9/20* (2006.01)
*A61K 9/00* (2006.01)
*A61K 31/616* (2006.01)

(52) U.S. Cl.
CPC ............ *A61K 9/2027* (2013.01); *A61K 9/0056* (2013.01); *A61K 31/616* (2013.01)

(58) Field of Classification Search
CPC . A61K 31/616; A61K 9/2027; A61K 9/0056; A61K 9/2054
See application file for complete search history.

(56) References Cited

U.S. PATENT DOCUMENTS

| | | | |
|---|---|---|---|
| 3,094,464 A * | 6/1963 | Joullie et al. | 424/469 |
| 4,327,076 A | 4/1982 | Puglia et al. | |
| 4,327,077 A | 4/1982 | Puglia et al. | |
| 4,775,536 A | 10/1988 | Patell | |
| 4,800,087 A | 1/1989 | Mehta | |
| 4,851,226 A | 7/1989 | Julian et al. | |
| 4,970,081 A | 11/1990 | Frisbee | |
| 5,026,559 A * | 6/1991 | Eichel et al. | 424/458 |
| 5,041,430 A | 8/1991 | Addicks et al. | |
| 5,068,110 A | 11/1991 | Fawzi et al. | |
| 5,489,436 A | 2/1996 | Hoy et al. | |
| 5,948,818 A | 9/1999 | Buser et al. | |
| 6,010,719 A | 1/2000 | Remon et al. | |
| 6,235,311 B1 | 5/2001 | Ullah et al. | |
| 6,663,896 B1 | 12/2003 | Blum | |
| 6,764,696 B2 | 7/2004 | Pather et al. | |
| 8,057,820 B2 | 11/2011 | Shah et al. | |
| 2002/0142034 A1 | 10/2002 | Shimizu et al. | |
| 2004/0110661 A1 | 6/2004 | Dietrich et al. | |
| 2006/0078611 A1 | 4/2006 | Shah et al. | |

FOREIGN PATENT DOCUMENTS

| | | |
|---|---|---|
| GB | 1544167 | 6/1977 |
| GB | 2104063 A | 4/1982 |
| WO | WO 99/47126 | 9/1999 |
| WO | WO 03/007917 | 1/2003 |

OTHER PUBLICATIONS

Lachman, "The Theory and Practice of Industrial Pharmacy", Chapter 11, ($3^{rd}$ edition 1986).

Leiberman, Pharmaceutical Dosage Forms—Tablets, vol. 2, $2^{nd}$ edition, 1990, pp. 213-217, 327-329, Marcel Dekker Inc.

Yuan et al., "The Effects of Alternating Combinations of an Enteric Coating and HPMC . . . " Pharmaceutical Technology, Nov. 2003, pp. 1-7.

* cited by examiner

*Primary Examiner* — Aradhana Sasan
(74) *Attorney, Agent, or Firm* — Laura A. Donnelly

(57) ABSTRACT

The invention relates to a tablet capable of being chewed or disintegrated in the oral cavity, which comprises an enteric coated aspirin active ingredient, and preferably a lightly compressed matrix comprising directly compressible carbohydrate(s) and at least one sweetener.

2 Claims, No Drawings

CHEWABLE ENTERIC COATED ASPIRIN TABLETS

RELATED APPLICATION

This application claims priority to U.S. application Ser. No. 10/961,563, filed on Oct. 8, 2004, the entire contents of which are incorporated herein by reference.

The present invention relates to a chewable or disintegrative tablet comprising enteric coated aspirin particles, preferably compressed into tablet form using dextrose monohydrate, and sucralose.

BACKGROUND OF THE INVENTION

Pharmaceuticals intended for oral administration are typically provided in solid form as tablets, capsules, pills, lozenges, or granules. Tablets are swallowed whole, chewed in the mouth, or dissolved in the oral cavity. Chewable or disintegrative tablets are often employed in the administration of pharmaceuticals where it is impractical to provide a tablet for swallowing whole, for instance with pediatric patients. In addition, with chewable tablets, the act of chewing helps to break up the tablet particles as the tablet disintegrates and may increase the rate of absorption by the digestive tract.

Workers in the field continue to try to improve the flavor and mouthfeel of chewable tablets and other comestibles. For instance, U.S. Pat. No. 4,327,076 to Puglia et al. relates to a chewable tablet formed of particles of active ingredient isolated from other ingredients of the tablet by admixing those particles with particles formed of an edible fat or oil absorbed on a fat-absorbing material, such as microcrystalline cellulose. The particles are blended with one or more tablet bonders, such as dextrose monohydrate. In addition, the tablet may also comprise other conventional ingredients, such as sweeteners.

U.S. Pat. No. 4,327,077 to Puglia et al. also relates to a chewable tablet. The tablet comprises particles of a recrystallized fatty material such as chocolate, a bulking material such as sugar or an active ingredient bound up in the particles of recrystallized fatty material, and a direct compaction vehicle that may be dextrose monohydrate.

PCT Application No. WO 99/47126 discloses compressed tablets capable of rapidly dissolving in aqueous solutions, comprising at least one non-saccharide water soluble polymer such as polyvinylpyrrolidone, optionally a saccharide of low moldability such as glucose, optionally a saccharide of high moldability such as maltose, sorbitol or a mixture thereof, and optionally a sweetener such as sucralose. These tablets are prepared by wet granulation, specifically a) granulating a formulation comprising the non-saccharide, water soluble polymer and active ingredient using no organic solvents, (b) compressing this into tablet form, (c) humidifying the tablet by exposing it to an aerated environment having at least about 50 to 100% relative humidity, and (d) drying the tablet.

Chewable tablets are known. U.S. Pat. No. 5,489,436 describes a chewable tablet made from a coated medicament wherein the coating comprises a mixture of dimethylaminoethyl methacrylate, a neutral methacrylic acid ester and a cellulose ester. The coating is described as a reverse enteric coating, which is not water soluble in non-acidic conditions but is soluble in acidic conditions. U.S. Pat. No. 4,851,226 describes a chewable medicament tablet made from coated granules of medicament wherein the coating on said granules comprises a blend of cellulose acetate or cellulose acetate butyrate and polyvinyl pyrrolidone. U.S. Pat. No. 4,800,087 describes a microencapsulating polymer for coating a pharmaceutical core that is capable of taste-masking the active compound. The polymer is described as maintaining its integrity when tabletted and/or chewed and can provide immediate release of the active compound in the stomach, or can release the active ingredient in the upper intestinal tract or in a sustained release fashion. U.S. Pat. No. 4,970,081 describes rapidly disintegrating aspirin tablets wherein the aspirin granules have been coated to provide a zero order release of the active ingredient.

It is also known that pharmaceutically active ingredients can be provided with enteric coatings. Providing enteric coatings on the active ingredient for aspirin, however, presents a number of unique challenges due to potential hydrolysis of the active to produce free salicylic acid. Several patents have been published that allegedly describe stabilized enteric-coated aspirin compositions, such as U.S. Pat. No. 4,900,559, which describes a stabilized enteric coated aspirin granules product prepared by commingling the enteric coated aspirin granule with glutamic acid hydrochloride. U.S. Pat. No. 5,068,110 allegedly improves the stability of an enteric-coated dosage form through the application of higher levels of coatings or by the application of higher levels of coatings in combination with the use of a protective coating.

Acid-labile actives, enteric coated and non-enteric coated, have been formulated as orally disintegratable tablets. For example, published PCT application WO 03/007917 describes a dosage form for enteric coated proton pump inhibitors in the form of a multi-particulate tablet that disintegrates in the mouth. Published U.S. Patent application 2004/0110661 describes a rapidly disintegrating tablet for acid-labile active ingredients. The tablet is described as comprising a plurality of individual active ingredient units together with excipients, wherein the acid-labile active is present in individual active ingredient units in a matrix composed of a mixture of a solid paraffin and one or more of a fatty alcohol, triglycerides and fatty acid ester. Published U.S. Patent application 2002/0142034 describe an orally disintegrable tablet that comprises fine granules having an average particle diameter of 400 μm or less.

There remains a need for a pharmaceutical product that can be chewed or that disintegrates in the mouth, which contains an enteric-coated aspirin active ingredient.

SUMMARY OF THE INVENTION

The present invention provides a tablet capable of being chewed or disintegrated in the oral cavity prior to swallowing, comprising enteric-coated aspirin particles, and preferably a matrix comprising directly compressible sugars or sugar-alcohols and high intensity sweetener, said tablet containing less than 5% fat and said matrix being substantially free of non-saccharide, water soluble polymeric binders.

DETAILED DESCRIPTION OF THE INVENTION

The tablet is made from a mixture comprising enteric-coated aspirin particles, preferably using directly compressible sugars or sugar-alcohols, together with high intensity sweeteners, and preferably the tablet has a sweetness index greater than about 1.0.

The enteric-coated aspirin is present in the tablet in a therapeutically effective amount, which is an amount that produces the desired therapeutic response upon oral administration and can be readily determined by one skilled in the art. In determining such amounts, the particular active ingredient being administered, the bioavailability characteristics of the active ingredient, the dose regime, the age and weight of the patient, and other factors must be considered, as known in the art.

The active ingredient is in form of particles, typically have an average particle size of about 1 micron to about 2000 microns. In one embodiment, the active ingredient particles are crystals having an average particle size of about 1 micron to about 1500 microns, e.g. from about 20 to about 1000 microns. In another embodiment, the active ingredient particles are granules or pellets having an average particle size of about 50 microns to about 2000 microns, e.g. about 50 microns to about 1000 microns, or about 100 microns to about 800 microns. As used herein, granules or pellets are typically agglomerates comprising a plurality of active ingredient crystals, and optionally excipients such as binders.

In one embodiment, the active ingredient is in the form of a large crystal, and typically has an average particle size from about 20 to about 1000 microns. Preferably, the active ingredient has an average particle size from about 50 to about 700 microns, and more preferably the active ingredient has an average particle size from about 100 to about 500 microns.

The thickness of the enteric coating on the active ingredient-containing core particle is typically from about 1 micron to about 20 microns, e.g. from about 2 microns to about 15 microns or from about 4 to about 9 microns.

Particles coated with an enteric coating, in a dried state, generally contain the enteric coating in an amount, based upon the total weight of particle and the enteric coating, from about 1 percent to about 50 percent, e.g. from about 15 percent to about 25 percent. The exact proportions of the coating to the active ingredient can vary depending upon, for example, the level of taste masking required. In embodiments employing a granulated particle, such as a rotogranulated particle, the active ingredient will constitute from about 5 to about 90 weight percent of the particle, with the remainder being the binder or filler. Suitable binders for the granulated particles include polyvinyl pyrrolidone, hydroxypropylmethyl cellulose, hydroxypropyl cellulose, and other pharmaceutically acceptable polymers. Fillers suitable for use in such granulated particles include lactose, confectioner's sugar, mannitol, dextrose, fructose, other pharmaceutically acceptable saccharide and microcrystalline cellulose.

In the practice of the present invention the enteric coating solution used to form the enteric coating layer on the tablets will comprise a water-soluble or water dispersible film forming enteric polymer dissolved or dispersed in an aqueous vehicle. A number of such film forming enteric polymers are known in the prior art that will serve the present purposes. At least three aqueous enteric polymer coatings are commercially available, Eudragit L30D (methacrylic acid-methacrylic acid ester copolymer marketed by Rohm-Haas GmBH, West Germany), Aquateric, a cellulose acetate phthalate-containing product marketed by FMC Corporation, Philadelphia, Pa. and Coateric (a polyvinyl acetate phthalate-based product marketed by Colorcon, Inc., West Point, Pa.). These will have conventional solubility characteristics of enteric polymers i.e. they will be insoluble in acid but will be soluble in a neutral-to-nearly alkaline medium.

One class of enteric polymers that are particularly suitable for the purpose of this invention is water-soluble or water dispersible acrylic resins. Of special interest in this regard is a polymer sold under the trade name Eudragit L30D. This is a copolymer that is anionic in character and based on polymethacrylic acid and acrylic acid esters. This is described by the formula:

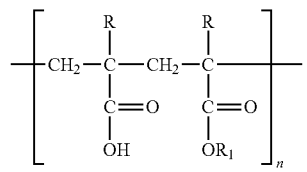

wherein: n is a number,
R is H or $CH_3$ and
$R_1$ is $CH_3$ or $C_2H_5$,
the ratio of free carboxyl group to ester groups is 1:1 and the mean molecular weight of the polymer is about 250,000.

The coating solution used to prepare the enteric coating layer on the tablets according to this invention may contain the enteric polymer formed from a high concentration aqueous system. In general this will amount to about 20% to about 35% by weight of enteric polymer based on the total weight of the coating solution with the preferred range being from about 25% to about 32% on the same weight basis, most preferably about 30%. Another important feature of this invention is the requirement for having a large weight gain of more than 25%, preferably more than 30% weight gain. The coating solution can further contain conventional plasticizers such as triethyl citrate, diethyl phthalate, tributyl citrate, triacetin, dibutyl phthalate, dibutyl sebecate, Myvacet 940, polyethylene glycol and other commonly used plasticizers as may be suitable for particular enteric polymers can be used.

The active ingredient is contained in a matrix comprising one or more edible carbohydrates such as dextrose monohydrate, mannitol, lactose, sucrose, erythritol, sorbitol, xylitol and other commonly used carbohydrates suitable for making tablets capable of being chewed or disintegrated in the oral cavity prior to swallowing. The amount of edible carbohydrate in the tablet is typically about 15 to about 90% by weight, preferably about 25 to about 85% by weight, and more preferably about 30 to about 75% by weight of the total weight of the tablet. The matrix also comprises one or more high intensity sweeteners.

The dosage form of the invention is a chewable or orally disintegratable tablet wherein the active ingredient is contained in a matrix comprising conventional, pharmaceutically acceptable excipients, such as fillers, conventional dry binders, sweeteners, disintegrants, and lubricants such as, for example, stearic acid, magnesium stearate, and mixtures thereof. Suitable fillers for chewable or orally disintegratable tablets include water-disintegratable, edible carbohydrates such as, for example, sugars, sugar alcohols, starch hydrolysates, and mixtures thereof. Examples of suitable sugars include, but are not limited to dextrose, sucrose, maltose, and lactose. Examples of suitable sugar alcohols include, but are not limited to mannitol, sorbitol, maltitol, xylitol, and erythritol. Examples of suitable starch hydrolysates include, but are not limited to, dextrins and maltodextrins.

In one embodiment, the water-disintegratable, compressible carbohydrate may be selected from dextrose monohydrate, mannitol, sorbitol, xylitol, and mixtures thereof. In embodiments in which a water-disintegratable compressible carbohydrate is employed as a filler, it is typically present at a level from, based upon the total weight of the dosage form, from about 40 to about 90 percent, e.g. from about 50 to about 80 percent.

The matrix may also incorporate pharmaceutically acceptable adjuvants, including, for example, preservatives, flavors such as, for example, orange and/or vanilla, acidulants, glidants, surfactants, and coloring agents such as, for example, FD&C yellow. However, the matrix preferably comprises no more than, based upon the total weight of the dosage form, about 25 weight % of such optional auxiliary ingredients.

The amount of edible carbohydrate in the tablet is typically about 15 to about 90% by weight, e.g. about 25 to about 85% by weight, say about 30 to about 75% by weight of the total weight of the tablet.

Intense sweetener compounds suitable for use herein include water-soluble artificial sweeteners such as 1,2-benzisothiazol-3 (2H)-one 1,1-dioxide (saccharin and its salts), cyclohexylsulfamic acid (cyclamate and its salts), and the potassium salt of 6-methyl-1,2,3-oxathiazin-4 (3H)-one-2,2-dioxide (Acesulfame-K, a commercially available product from Hoechst Celanese Corporation, Somerville, N.J.), proteins such as thaumatin (Talin, a commercially available product of Tate & Lyle Products, Reading, United Kingdom), chlorodeoxysugar derivatives (such as Sucralose, a commercially available product of Tate & Lyle), and dipeptides such as N-L-alpha-aspartyl-L-phenylalanine I-methyl ester (Aspartame, a commercially available product of the Nutrasweet Company, Deerfield, Ill.) and L-alpha-aspartyl-D-alanine N-(2,2,4,4-tetramethyl-3-thietanyl)amide (Alitame, a commercially available product of Pfizer, New York, N.Y.), and dihydrochalcones . . . . The amount of high intensity sweetener in the tablet is typically about 0 to about 20% by weight, preferably about 0.01 to about 5% by weight, and more preferably about 0.1 to about 3% by weight of the total weight of the tablet.

In a preferred embodiment, the chewable or orally disintegratable tablet of the present invention has a sweetness index greater than about 1.0. Sweetness index is an indication of the relative sweetness of a material with respect to that of sucrose. Sucrose is used as the standard, with a sweetness index of 1.0. Dextrose (glucose) has a sweetness index of about 0.6, which is it is about 60% as sweet as sucrose. Sucralose, a high intensity sweetener, has a sweetness index of about 600, that is, it is about 600 times as sweet as sucrose. The sweetness index of the tablet can be calculated as a weighted sum of all the sweetening ingredients in the tablet, i.e. the sum of the mass fraction of each ingredient times its sweetness index. Those skilled in the art will recognize that the presence of a high-intensity sweetener is necessary in order to make a chewable or orally disintegratable tablet having a sweetness index greater than 1.0.

In one particular embodiment, the edible carbohydrate is dextrose monohydrate and the high intensity sweetener is sucralose. Sucralose, 4,1'6'-trichloro-4,1,6'-trideoxy-galactosucrose, is a high intensity sweetener manufactured from sucrose as a starting material. This and other chlorine-substituted sucrose sweeteners are disclosed in British Patent No. 1,544,167, and in British Patent Application No. 2,104,063A. In embodiments employing sucralose as the high intensity sweetener, the amount of sucralose in the tablet is typically about 0.005 to about 10% by weight of the total weight of the tablet, preferably about 0.01 to about 5% by weight, and more preferably about 0.5 to about 2% by weight of the total weight of the tablet. Preferably, the weight ratio of dextrose monohydrate to sucralose in the tablet is at least about 25:1, more preferably at least about 50:1, most preferably at least about 75:1. Preferably, the dextrose monohydrate is present in the tablet in directly compressible form. That is, the dextrose monohydrate has an average particle size of about 100 to about 500 microns, e.g. about 100 to about 250 microns, say about 150 to about 200 microns. Such a particle size is useful to impart the formulation with adequate flowability and compressibility, and with a smooth and creamy mouthfeel.

The amount of edible carbohydrate in the tablet is typically about 15 to about 90% by weight, preferably about 25 to about 85% by weight, and more preferably about 30 to about 75% by weight of the total weight of the tablet.

The use of directly compressible carbohydrate at these levels enables the minimization or elimination of cellulosic dry binders such as microcrystalline cellulose from the formula. The avoidance of microcrystalline cellulose improves both the taste and the mouthfeel of the resulting tablets. While it may be desirable to use microcrystalline cellulose at relatively low levels in the formulation for its disintegrant properties, the higher levels generally used for binding properties are not necessary. The amount of microcrystalline cellulose in the tablet is preferably less than about 20% by weight, more preferably less than about 10% by weight of the tablet, and most preferably, the tablet is substantially free of microcrystalline cellulose.

The use of directly compressible carbohydrates at these levels advantageously enables the minimization or elimination of fat. Fats are generally understood to mean esters of glycerol and fatty acids, which can include monoglycerides, diglycerides, and triglycerides. Preferably, the tablet of the present invention contains less than about 5% fat. More preferably, the tablet contains less than about 3% by weight of fat, most preferably the tablet contains substantially no fat. Fat-free formulations are more stable at elevated temperatures, eliminating the need for specially controlled shipping and storage conditions. Additionally, fats are susceptible to oxidative and chemical hydrolysis, leading to a "rancid" taste and/or odor. This effectively shortens the shelf life of a product. Preferably the melting point of any fats or other oily materials that are included in the composition is greater than about 80° F. in order to maintain product stability at elevated temperatures during shipping or storage.

In a particularly preferred embodiment of the invention the tablet is substantially free of tri-glycerides specifically. Triglycerides are more hydrophobic than mono- and di-glycerides, and are expected to hinder dissolution of the active ingredient. This is undesirable in an immediate release dosage form such as the tablet of this invention.

The tablet may contain other conventional ingredients, such as fillers, conventional dry binders, other sweeteners, disintegrants, and lubricants. The mixture may also incorporate pharmaceutically acceptable adjuvants, including, for example, preservatives, flavors, acidulants antioxidants, glidants, surfactants, and coloring agents. However, the tablet preferably comprises no more than about 25 weight % of such optional auxiliary ingredients.

The tablet may be made in any manner, and a variety of tableting methods are known in the art. Conventional methods for tablet production include direct compression ("dry blending"), dry granulation followed by compression, and wet granulation followed by drying and compression. Other methods include the use of compacting roller technology such as a chilsonator or drop roller, or molding, casting, or extrusion technologies. All of these methods are well known in the art, and are described in detail in, for example, Lachman, et al., *The Theory and Practice of Industrial Pharmacy*, Chapter 11, ($3^{rd}$ Ed. 1986).

Preferably the tablets are formed by the direct compression method, which involves directly compacting a blend of the enteric-coated aspirin, dextrose monohydrate, sucralose, and any other appropriate optional ingredients. After blending, a pre-determined volume of particles is filled into a die cavity of a rotary tablet press, which continuously rotates as part of a "die table" from the filling position to a compaction position. The particles are compacted between an upper punch and a lower punch to an ejection position, at which the resulting tablet is pushed from the die cavity by the lower punch and guided to an ejection chute by a stationary "take-off" bar. The direct compression process enables the minimization or elimination of water-soluble, non-saccharide polymeric binders such as polyvinyl pyrrolidone, alginates, hydroxypropyl cellulose, hydroxypropylmethylcellulose, hydroxyethylcellulose, and the like, which can have an adverse effect on dissolution.

Preferably, tableting is carried out such that the tablet is relatively soft. The hardness of the tablet is preferably up to about 15 kiloponds per square centimeter ($kp/cm^2$). More preferably, the hardness of the tablet is in the range of about 1 to 8 $kp/cm^2$, most preferably about 2 to 6 $kp/cm^2$. Hardness is a term used in the art to describe the diametral breaking strength as measured by conventional pharmaceutical hardness testing equipment, such as a Schleuniger Hardness Tester. In order to compare values across different size tablets, the breaking strength is normalized for the area of the break (which may be approximated as tablet diameter times thickness). This normalized value, expressed in $kp/cm^2$, is sometimes referred in the art as tablet tensile strength. A general discussion of tablet hardness testing is found in Leiberman et al., *Pharmaceutical Dosage Forms—Tablets*, Volume 2, $2^{nd}$ ed., Marcel Dekker Inc., 1990, pp. 213-217, 327-329.

In another embodiment the tablet may be made using a process designed to produce a freeze-dried foam dosage form. A freeze-dried dosage form is produced by forming a dispersion of a gas and a suspension of a bulk forming agent and the enteric coated active ingredient. The bulk forming agent includes such materials as long chain polymers, e.g. polypeptides such as gelatin or hydrolyzed gelatin, cellulose derivatives, alginate derivatives, polyvinylpyrrolidone, polyethylene glycols, polysacharides such as dextrin, mannitol, sugars and starches, and gums such as acacia, xanthan, and tragacanth. Surfactants such as sodium lauryl sulfate, polyoxyethylene sorbitan esters, sorbitan esters, lecithin, sodium dioctylsulphosuccinate and other conventionally used surfactants may be added to the solution or suspension to stabilize the foam formed during the dispersion phase. Other optional ingredients may be added to the solution or suspension such as acidulants, sweeteners, colorants or flavors. The solution or suspension may be dispensed into preformed molds, cavities or packaging; or deposited in a drop-like fashion in order to form the tablets. The resulting solution or suspension is then freeze dried by a conventional freeze drying process. These tablets dissolve rapidly in the oral cavity upon ingestion.

Specific embodiments of the present invention are illustrated by way of the following examples. This invention is not confined to the specific limitations set forth in these examples, but rather to the scope of the appended claims. Unless otherwise stated, the percentages and ratios given below are by weight.

Example for Aspirin Chewable Containing Enteric Coated Crystals

Example 1

Preparation of Enteric Release Coating Solution

A coating dispersion is prepared by dispersing Methyl citrate and anionic copolymer of methacrylic acid and methacrylates (Eudragit L-30D) under ambient conditions, so that the finished dispersion contains 31.6% by weight of the coating materials. The relative amounts of coating materials are, based upon the total weight percent of the final coating,

| | |
|---|---|
| Triethyl Citrate | 7.4% |
| Eudragit L-30D* (30% Solid dispersion) | 92.6% |

*available from Rohm Pharma, Inc.

Example 2

Preparation of Coated Active Ingredient

Preparation of Coated Aspirin:

5000.0 g of aspirin crystals are coated with the enteric release solution described in Example 1 at a spray rate of about 70-83 g/min in a Glatt GPCG-5/9 fluid bed unit with a top-spray insert under product temperature conditions of about 32-35° C. and an atomization air pressure of 3 bar. The resulting coated aspirin contain, based upon the total dry weight of the coated aspirin and the enteric release coating, about 35% of the enteric release coating.

Example 3

Production of Tablets for Evaluation Thereof

Preparation of the Tablet Blend Base

| Ingredients | Percent (w/w) | mg/tab |
|---|---|---|
| Coated Aspirin (65% active) | 16.36 | 126.00 |
| Saccharin NF | 0.52 | 4.00 |
| Crospovidone NF | 1.65 | 12.70 |
| Orange Flavor | 0.52 | 4.00 |
| Stearic Acid NF | 1.97 | 15.20 |
| Dextrose Monohydrate NF | 78.90 | 607.50 |
| Lake Color | 0.08 | 0.60 |
| TOTAL | 100.0 | 770.00 |

The materials in the table above are blended using the following procedure. All materials are manually passed through a 30 mesh screen. The materials are placed into a 4-quart V-Blender and mixed for 5 minutes.

Preparation of Compressed Tablets

To prepare the chewable tablet, the tablet base blend is compressed on a rotary tablet press. The tablets are compressed at a weight of 770 mg with a hardness range of 3-9 kiloponds.

Example 4

Analysis of Dissolution Data

All dissolutions for aspirin are analyzed using the following dissolution analysis: USP Type I apparatus (baskets, 100 RPM) in 0.1N hydrochloric acid solution (acid stage) at 37° C. for 120 minutes and at pH 6.8 phosphate buffer (buffer stage) at 37° C. for an additional 90 minutes. Approximately 20 mL samples are tested at 120 minutes in the acid stage and at an additional 90 minutes in the buffer stage for aspirin quantity. Dissolution samples are analyzed for aspirin versus a standard prepared at the theoretical concentration for 10% released for the acid stage timepoint and 100% released for the buffer stage timepoint. Samples are analyzed using a Agilent® UV spectrophotometer set at a wavelength of 280 nm for the acid stage using a 3 cm flow-cell, and at a wavelength of 265 nm for the buffer stage using a 1 cm flow-cell.

We claim:

1. A process for preparing a chewable tablet comprising applying an enteric coating onto aspirin particles, wherein said enteric coating is formed from a dispersion of triethyl citrate and an anionic copolymer of methacrylic acid and methacrylates, and compressing said enteric-coated aspirin particles into tablet form, wherein said aspirin particles are not granulated during processing, and wherein said aspirin particles comprise a matrix comprising (a) about 75% to about 90% by weight of dextrose monohydrate, and (b) about 0.05% to about 2.0% saccharin.

2. A process according to claim 1 wherein the enteric coating weight gain is at least 20%.

* * * * *